United States Patent [19]
Kankaras

[11] 3,988,001
[45] Oct. 26, 1976

[54] VARIABLE FLOW CONTROL VALVE FOR USE WITH DENTAL SYRINGES AND THE LIKE

[75] Inventor: Rajko Kankaras, Rochester, N.Y.

[73] Assignee: Sybron Corporation, Rochester, N.Y.

[22] Filed: July 21, 1975

[21] Appl. No.: 597,547

[52] U.S. Cl. .............................. 251/227; 251/228; 251/251; 251/298
[51] Int. Cl.² ................. F16K 25/00; F16K 31/524
[58] Field of Search .......... 251/298, 251, 228, 215, 251/226, 227

[56] References Cited
UNITED STATES PATENTS

| | | | |
|---|---|---|---|
| 2,526,457 | 10/1950 | Bradbury | 251/228 X |
| 2,622,435 | 12/1952 | Lucas et al. | 251/228 X |
| 2,934,902 | 5/1960 | Anderson | 251/298 X |
| 2,984,452 | 5/1961 | Hooper | 251/228 |

FOREIGN PATENTS OR APPLICATIONS
168,360   5/1951   Austria ........................... 251/228

Primary Examiner—Arnold Rosenthal
Attorney, Agent, or Firm—Theodore B. Roessel; Roger Aceto

[57] ABSTRACT

A valve for dental syringes and the like has its actuator provided with a cam. When the actuator is moved axially it engages a valve seal member and rocks the member on the valve seat so that initially only a portion of the valve about the periphery of the valve seal member is open. Moving the actuator further causes the entire valve seal member to move off of the valve seat so that the full circumference about the seal member is opened. The rocking of the valve seal member on the seat and then moving it axially from the valve seat provides substantially linear volume control from zero flow to the designed maximum flow of the valve.

11 Claims, 5 Drawing Figures

VARIABLE FLOW CONTROL VALVE FOR USE WITH DENTAL SYRINGES AND THE LIKE

BACKGROUND OF THE INVENTION

The present invention relates generally to valves and more specifically to valves as may be used in dental syringes and the like.

For many applications, and in particular dental syringes, a valve is needed which is activated by axially pushing the valve actuator. It is also important for dental applications that the dentist have close control of the fluid flow from the syringe from zero flow to the designed maximum flow of the valve. These two features heretofore have been difficult to reconcile in valves of the prior art. In many valves of the prior art where the valve seal member is moved axially from the valve seat, the entire circumference of the valve is open to accommodate the fluid flow. Accordingly, in this type of prior art valve, it was necessary to maintain close, critical tolerances between the opening of the valve seat and the valve member. Not only is it expensive to maintain such close tolerances as required in such a valve but, the valve member itself must be hardened as any wear reduces the amount of control over the flow which can be exercised by the dentist. All these factors added considerably to the cost of the valve.

The valve of the present invention not only allows for a greater control of flow than valves of the prior art, but also accomplishes this control while utilizing considerably less critical tolerances which in turn greatly reduces cost. Further, since the tolerances are reduced, wear becomes less of a factor so that the life of the valve is prolonged.

Another troublesome problem with dental syringes is that when the actuator is released and the valve closed, some liquid remains and/or drips from the nozzle of the syringe. There is the danger of any fluid, such as water, remaining in the nozzle becoming contaminated and of course any dripping from the nozzle is objectionable in that it wets the exterior of the dental equipment.

In the valve of the present invention, a slight negative pressure is created when the valve actuator is releaased so that when the valve is closed, fluid is drawn from the nozzle and back into the valve housing where there is less likelihood of contaminaation and dripping is prevented.

The aforementioned features of the present invention are accomplished by tilting the valve member on, and with respect to, its seat responsive to the initial axial movement of the valve actuator. This opens only a portion of the total circumference of the valve to fluid flow. Continuing the axial movement of the actuator then drives the entire valve member from its seat to open the entire circumference of the valve to fluid flow. Still further movement of the actuator drives the valve member entirely from the seat to provide the maximum valve opening. On release of the actuator, the valve member is returned to its seat to close the valve. A bias means continues to operate on and move the actuator after the valve member is seated. This provides a suction which draws fluid from the nozzle back into the valve housing.

SUMMARY OF THE INVENTION

The present invention may be characterized in one aspect thereof by the provision of a generally cylindrical valve housing having an inlet and an outlet and a valve seat intermediate the inlet and outlet; a valve member including a bias means to urge the valve member against the seat, the valve member having a portion provided with a cam follower; an axially movable actuator having a cam surface thereon engaging the cam follower portion of the valve member, the axial movement of the actuator causing the cam surface to engage the cam follower to tilt the valve member on its seat to partly open the valve and continued axial movement of the actuator moves the valve member from its seat to completely open the valve.

OBJECT OF THE INVENTION

One object of the present invention is to provide a valve for dental syringes and the like which allows an almost linear volume control of fluid flow from zero flow to the design maximum.

Another object of the present invention is to provide a valve for dental syringes and the like wherein axial movement of the valve actuator initially tilts the valve member with respect to the valve seat and thereafter moves the valve member from the seat.

Still another object of the present invention is to provide a valve for a dental syringe or the like which greatly reduces the tolerances required between the valve member and the opening of the valve seat.

A further object of the present invention is to provide a valve for dental syringes and the like wherein a negative pressure is created within the valve housing upon release of the actuator so as to present the escape of fluid from the nozzle of the valve when the valve is closed.

A still further object of the present invention is to provide a valve for dental syringes and the like which is economical to manufacture and simple to install and replace.

These and other objects of the present invention will become more apparent upon consideration of the following detailed description thereof when taken in connection with the accompanied drawing depicting the same.

DESCRIPTION OF THE PREFERRED EMBODIMENTS

Figures 1, 2:
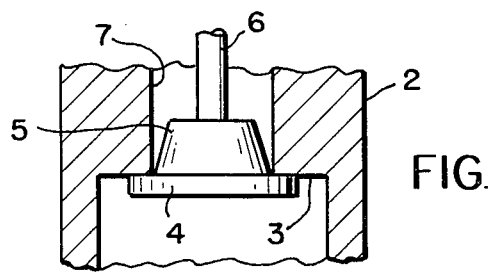
FIG. 1 is a schematic presentation of a typical prior art valve.
FIG. 2 is a cross-sectional view of the valve of the present invention in a closed position.

Referring to the drawing, FIG. 1 labeled prior art shows a portion of a typical flow control valve for dental syringes and the like. The valve includes a housing 2 having a annular valve seat 3. Flow of the fluid is upward through the valve as viewed in the figure. The valve seat is sealed by a gasket 4 fixed to a valve member 5. Opening the valve is accomplished by simply moving the stem 6 of the valve member axially downward as viewed in the figure so that the entire periphery about the valve member is open to fluid flow. In one prior art valve, the diameter of the valve opening 7 was 0.1390 inches and the maximum outside diameter of valve member 5 was 0.1387 inches. The tolerances in both cases was plus or minus 0.0001 inches. Thus, the clearance between valve member and valve opening is only 0.0003 inches. These close tolerances required careful machining and hardening of the various elements of the valve so as to reduce wear as much as possible. Consequently, this prior art valve was relatively expensive to manufacture.

FIG. 2 shows the valve of the present invention generally indicated at 10. In this valve, the diameter of the valve opening has been kept at 0.139 inches while reducing the maximum diameter of the valve member to 0.132 inches and most importantly, reducing the tolerances in both cases to 0.007 inches. As shown in the figure, the valve includes a valve housing 12 designed for insertion into a bore 18 in the dental syringe 20. For purposes of the present invention, it is not necessary to show the entire dental syringe and is sufficient merely to illustrate the position of the valve in the syringe and the fluid inlet and outlet paths 22, 24 respectively of the syringe. Thus, to assemble the valve housing to the syringe, it is merely inserted into one end of bore 18 and then threaded to an end cap 14. This anchors the valve in the syringe body 20. Located between valve housing 12 and syringe bore 18 are O-rings 26 which prevent leakage between the valve housing and the syringe bore.

Housing 12 has an inlet port 28 communicating with syringe inlet 22 and an outlet port 30 communicating with the syringe outlet 24. Furthermore, the valve housing is necked at 16 intermediate the inlet and outlet ports to define an annular valve opening 32 communicating with both the inlet and outlet ports. The lower end face 34 of this neck defines a valve seat.

Disposed within and extending through valve opening 32 is a floating valve member 36, that is, the valve member is not fixed to any other part of the valve. The lower portion of the valve member carries a resilient seal ring 38. Seal ring 38 is urged against the valve seat 34 by a spring 39 which is biased between the valve member and end cap 14. Thus, the spring urges valve member 36 and therefore, seal ring 38 upwardly as viewed in the figure so that under normal conditions, valve opening 32 is closed. The valve member has a body portion 40 disposed in the valve opening, the outer surface of this body portion being somewhat dome-shaped. Extending upward from the top of this dome is a cam follower 42 for purposes set out hereinbelow.

A valve actuator for opening the valve includes a manually operated push button 44 extending out from the syringe bore and a depending stem 46 extending into the valve housing 12. The depending stem has a cam surface 48 on its lower most face adapted to engage cam follower 42. The actuator moves axially in the valve housing and is normally biased in an upward direction as viewed in the figure by a spring 50 which is biased between valve housing 12 and a collar 52 on actuator stem 46. An O-ring 54 disposed about stem 46 between the collar and the valve housing provides a sliding seal between the actuator and the internal wall surface of the valve housing. When the valve actuator is in a normal position and the valve is closed as shown in FIG. 1, cam surface 48 is clear of, and axialaly removed from, cam follower 42.

Figure 3:
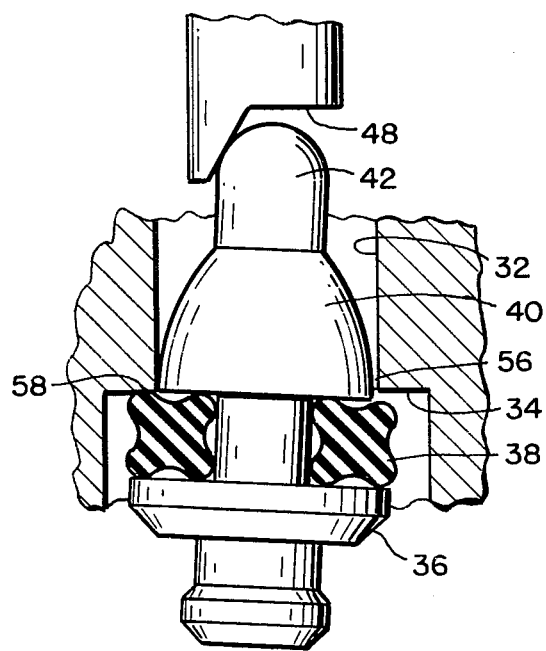
FIGS. 3 and 4 are views similar to FIG. 1 only showing a portion of the valve with the valve member in partly open positions.

In order to operate the valve, push button 44 is depressed to move the actuator axially against the bias of spring 50. This brings cam surface 48 into engagement with cam follower 42. Further axial movement of the push button will now cause the cam to tilt valve member 36 and move it slightly from its vertical orientation. This is shown in FIG. 3. As set out above, the body portion 40 of valve member 36 is somewhat dome-shaped. This allows the member to clear valve opening 32 when valve member 36 is tilted. As the valve member tilts, a portion of seal ring 38 is lifted from valve seat 34 to unseal a portion of the valve opening as shown at 56. The opposite side of seal ring 38 remains in engagement with seal seat 34 as shown at 58. When seen in plan view, the unsealed portion at 56 is generally cresent-shaped.

Figure 4:
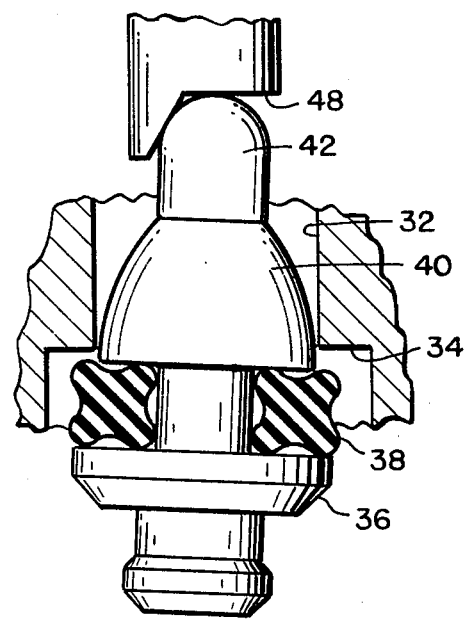

As the valve actuator continues to move axially, valve member 36 continues to tilt which moves more and more of resilient seal ring 38 from the seal seat. This continues until the seal ring has been completely removed from the seat as shown in FIG. 4. Further movement of the actuator will now simply drive valve member 36 against the bias of spring 39 and move the dome-shaped body 4 through valve opening 32 thereby increasing the cross-sectional open area of the valve opening available for fluid flow.

Figure 5:
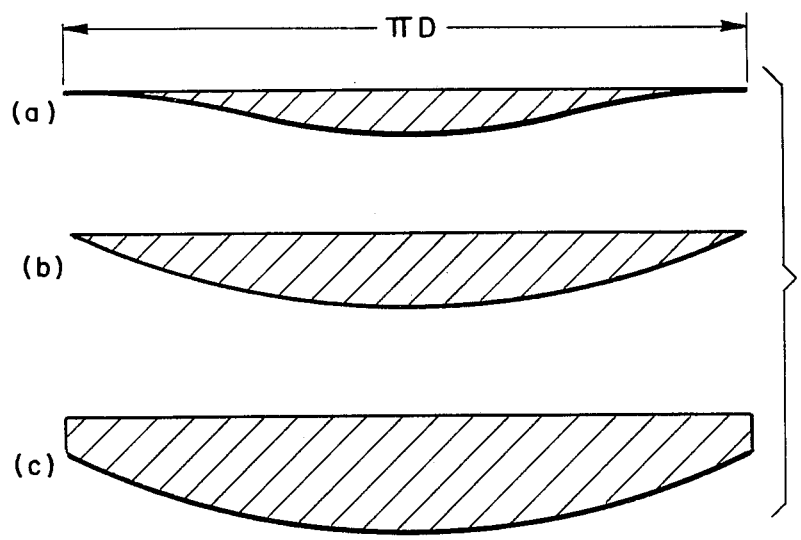
FIG. 5 shows graphic representations of the open crosssectional areas of the valve in various partly open and full open positions.

The area of the valve which becomes open as the actuator is depressed is shown schematically in FIG. 5. FIG. 5(a) shows that when the actuator is initially depressed, and valve member 36 tilted on its axis only a portion of the circumference of the valve opening is available for fluid flow. In FIG. 5(b), the actuator has been depressed to the point where seal ring 38 is completely removed from valve seat 34. FIG. 5(c) shows the cross-sectional area available for fluid flow when the actuator is fully depressed so as to move valve member 36 through valve opening 32. Here, the dome shape of the valve member body portion 40 together with the linear profile of valve opening 32 creates the greatest open area for fluid flow around the body portion and through the openings.

It should be appreciated while three distinct positions are represented by FIGS. 5(a), 5(b), and 5(c), these are only representative of three valve positions and that a more infinite range between the full open and full close position can be accomplished with the valve of the present invention.

As a further feature of the present invention, releasing push button 44 not only will close the valve, but also will draw any liquid remaining in syringe outlet 24 back into valve housing 12 so as to reduce or eliminate any drip of seepage from the outlet. In this respect, spring 39 will return valve member 36 to an initial position and reseat seal ring 38 against seal seat 34. Spring 50 likewise moves the actuating member (push button 44 and depending stem 46) back to its initial position. However, the actions of springs 39 and 50 are independent so that spring 50 continues to move the actuating member even after seal ring 38 is seated against seat 34. Since O-ring 54 provides a sliding seal against the internal surface of valve housing 12, this continued movement of the actuator creates a slight negative pressure in the portion of the valve housing between seal seat 34 and O-ring 54. This negative pressure empties the syringe outlet of liquid by drawing the liquid from syringe outlet 24 and back into the valve housing which in turn prevents any dripping of liquid from the outlet after the valve is closed. Thus, this negative pressure or suction is created by the extra travel of the actuator after the valve is closed, that is after seal ring 38 is seataed against seal seat 34.

Thus, it should be appreciated that the present invention accomplishes its intended objects in providing a valve for dental syringes and the like which provides substantially linear control of the fluid flow from zero flow to the designed maximum of the valve. The structure of the valve of the present invention also eliminates the need for relatively close tolerances between the various components of the valve and also provides a feature which prevents dripping of liquid from a syringe nozzle when the valve is closed.

Having thus described the invention in detail, what is claimed as new is:

1. In a valve for dental syringes and the like including a valve housing having an inlet and an outlet for fluid and an intermediate valve seat, a valve member in the housing and bias means for urging and valve member against the valve seat to close the valve, the valve seat, valve member and bias means being axially aligned, the improvement comprising:
    a. said valve member being both tiltable and axially movable with respect to said valve seat; and
    b. actuator means extending into said housing in axial alignment with said valve member, said means being movable axially and engagable with said valve member for first tilting said valve member with respect to said valve seat and thereafter moving said valve member axially from said valve seat against said bias.

2. A valve as in claim 1 including cooperating cam means on said valve member and actuator means for first tilting and thereafter axially moving said valve member with respect to said valve seat responsive to axial movement of said actuator means.

3. A valve as in claim 2 wherein said cam means includes a cam surface on said actuator means and a cam follower on said valve member.

4. A valve as in claim 1 wherein said valve seat is disposed about a valve opening which communicates with said inlet and outlet, said valve member having a dome-shaped portion disposed for movement through said opening, the outside diameter of the said portion at its widest being smaller than the inside diameter of said valve opening.

5. A valve for dental syringes and the like comprising:
    a. a valve housing having an inlet and an outlet for fluid, said valve housing defining a valve opening and a valve seat intermediate said inlet and outlet;
    b. a valve member in said housing extending axially through said valve opening;
    c. seal means on said valve member engagable with said valve seat;
    d. bias means urging said valve member in an axial direction towards said valve seat to seat said seal means thereagainst;
    e. actuator means axially aligned with said valve member including a stem portion extending into said housing, said actuator means being axially movable to engage said valve member; and
    f. cooperating cam means on said stem portion and valve member acting responsive to axial movement of said actuator means to first tilt and thereafter axially move said valve member with respect to said valve seat and against said bias means.

6. A valve as in claim 5 including a second bias means in said housing acting solely on said actuator means for urging the same axially away from said valve member after said seal means is seated against said valve seat.

7. A valve as in claim 6 including a sliding seal disposed about said stem and engaging said valve housing, said sliding seal and second bias means acting together to create a negative pressure in said valve housing after seating of said seal means against said valve seat, whereby upon closing of said valve fluid flows back through said outlet and into said valve housing.

8. A valve as in claim 5 wherein said valve member has an upstanding dome-shaped portion extending into said valve opening, the outside diameter of said dome portion being smaller than the inside diameter of said valve opening to permit said valve member to clear the sides of said opening when said valve member is tilted with respect to said valve seat.

9. A valve as in claim 5 wherein said cam means includes a cam surface on the lower most face of said depending stem and a cam follower on said valve member.

10. A valve as in claim 9 wherein said cam surface and cam follower are normally held spaced apart and engagement occurs upon axial movement of said actuator means.

11. A valve for dental syringes and the like comprising:
    a. a valve housing having a valve seat intermediate a fluid inlet and a fluid outlet;
    b. a valve member in said housing axially aligned with said seat;
    c. bias means urging said valve member against said seat;
    d. a cam follower on said valve member;
    e. actuator means arranged in said housing in axial alignment with said valve member said actuator means being axially movable and having a cam surface thereon for engaging said cam follower, the axial movement of said actuator and the engagement of said cam follower and cam surface causing said valve member to first tilt and then move axially with respect to said valve seat.

* * * * *

UNITED STATES PATENT AND TRADEMARK OFFICE
CERTIFICATE OF CORRECTION

PATENT NO. : 3,988,001
DATED : October 26, 1976
INVENTOR(S) : Rajko Kankaras

It is certified that error appears in the above–identified patent and that said Letters Patent are hereby corrected as shown below:

Column 1, line 44, correct the spelling of "released".

Column 2, line 31, correct the spelling of "prevent".

Column 3, line 65, correct the spelling of "axially".

Column 4, line 14, correct the spelling of "crecent".

Column 4, line 51, "of" should be "or".

Column 5, line 2, correct the spelling of "seated".

Column 5, line 19, change "and" to "the".

Signed and Sealed this

Fourth Day of January 1977

[SEAL]

Attest:

RUTH C. MASON
*Attesting Officer*

C. MARSHALL DANN
*Commissioner of Patents and Trademarks*